(12) United States Patent
Heiss

(10) Patent No.: US 6,652,551 B1
(45) Date of Patent: Nov. 25, 2003

(54) BILIARY SPHINCTER SCISSORS

(76) Inventor: Frederick W. Heiss, 112 Bartlett Hill, Concord, MA (US) 01742

(*) Notice: Subject to any disclaimer, the term of this patent is extended or adjusted under 35 U.S.C. 154(b) by 96 days.

(21) Appl. No.: 09/621,210

(22) Filed: Jul. 21, 2000

(51) Int. Cl.[7] ............................................. A61B 17/32
(52) U.S. Cl. ...................... 606/170; 606/167; 606/171; 606/174
(58) Field of Search ................... 606/167, 170, 606/171, 172, 173, 174; 128/305, 898

(56) References Cited

U.S. PATENT DOCUMENTS

| | | | |
|---|---|---|---|
| 2,541,246 A | * 2/1951 | Held | 606/205 |
| 4,407,273 A | 10/1983 | Ouchi | 128/6 |
| 4,729,374 A | * 3/1988 | Alfranca | 606/171 |
| 5,133,727 A | 7/1992 | Bales et al. | 606/170 |
| 5,152,772 A | * 10/1992 | Sewell, Jr. | 604/22 |
| 5,171,258 A | 12/1992 | Bales et al. | 606/205 |
| 5,192,298 A | 3/1993 | Smith et al. | 606/205 |
| 5,201,752 A | * 4/1993 | Brown et al. | 600/564 |
| 5,228,451 A | 7/1993 | Bales et al. | 128/751 |
| 5,293,878 A | 3/1994 | Bales et al. | 128/751 |
| 5,352,222 A | 10/1994 | Rydell | 606/37 |
| 5,352,235 A | 10/1994 | Koros et al. | 606/174 |
| 5,366,466 A | 11/1994 | Christian et al. | 606/174 |
| 5,392,789 A | 2/1995 | Slater et al. | 128/751 |
| 5,439,478 A | 8/1995 | Palmer | 606/205 |
| 5,445,638 A | 8/1995 | Rydell et al. | 606/51 |
| 5,478,351 A | 12/1995 | Meade et al. | 606/205 |
| 5,496,310 A | 3/1996 | Exconde et al. | 606/205 |
| 5,569,243 A | 10/1996 | Kortenbach et al. | 606/46 |
| 5,601,572 A | 2/1997 | Middleman et al. | 606/139 |
| 5,632,746 A | 5/1997 | Middleman et al. | 606/78 |

(List continued on next page.)

FOREIGN PATENT DOCUMENTS

| | | |
|---|---|---|
| DE | 19757 056 A1 | 7/1999 |
| DE | 19813 781 A1 | 10/1999 |
| EP | 0 537 574 A2 | 4/1993 |
| EP | 0 572 131 A1 | 12/1993 |
| EP | 0 734 682 B1 | 10/1996 |
| JP | 08 164141 A | 6/1996 |
| JP | 10 179602 A | 7/1998 |
| JP | 11 155870 A | 6/1999 |
| SU | 492274 A | 12/1975 |
| WO | WO 97/01305 | 1/1997 |
| WO | WO 97/42892 | 11/1997 |
| WO | WO 97/49342 | 12/1997 |
| WO | WO 99/17661 | 4/1999 |
| WO | WO 02/11621 | * 2/2002 |

OTHER PUBLICATIONS

Freeman, M. L., et al., "Complications of Endoscopic Biliary Sphincterotomy," *The New England Journal of Medicine*, 335 (*13*) :909–918 (Sep. 1996).

Kasmin, F. E., et al., "Needle–knife sphincterotomy in a tertiary referral center: efficacy and complications," *Gastrointestinal Endoscopy*, 44(*1*) :48–53 (1996).

"The How it Works Series," Part One through Part Six, *The FiberTech Newsletter* (1996).

Pentax "Video Endoscope System," (1995–1996).

Pentax "Owner's Manual for Video Duodenoscopes ED–3401 Ed–3410," pp. 1–29.

*Primary Examiner*—John J. Calvert
*Assistant Examiner*—Shaun R Hurley
(74) *Attorney, Agent, or Firm*—Bowditch & Dewey, LLP

(57) ABSTRACT

Biliary sphincter scissors, used in a sphincterotomy, include a stationary blade and an actuated blade having dimensions which allow the scissors to pass through a channel in an endoscope. The biliary sphincter scissors include a flexible arc-shaped curvature in the distal end to allow for creation of an incision in a sphincterotomy.

31 Claims, 16 Drawing Sheets

U.S. PATENT DOCUMENTS

| | | | |
|---|---|---|---|
| 5,741,285 A | 4/1998 | McBrayer et al. | 606/170 |
| 5,766,170 A | 6/1998 | Eggers | 606/48 |
| 5,769,849 A | 6/1998 | Eggers | 606/48 |
| 5,797,939 A | 8/1998 | Yoon | 606/167 |
| 5,797,958 A | 8/1998 | Yoon | 606/207 |
| 5,827,281 A | 10/1998 | Levin | 606/51 |
| 5,899,919 A | 5/1999 | Eubanks, Jr. et al. | 606/205 |
| 5,951,488 A | 9/1999 | Slater et al. | 600/564 |
| 5,961,514 A | 10/1999 | Long et al. | 606/41 |
| 5,984,920 A | 11/1999 | Steinbach | 606/47 |
| 6,017,339 A * | 1/2000 | Sadamasa | 606/46 |
| 6,017,340 A * | 1/2000 | Cassidy et al. | 606/110 |

* cited by examiner

BILIARY SPHINCTER SCISSORS

BACKGROUND OF THE INVENTION

Flexible fiberoptic and video endoscopes have permitted access through the duodenum for diagnostic and therapeutic biliary endoscopy. Therapeutic procedures usually require sphincterotomy for operations such as stone extraction and placement of stents.

To perform a safe and successful sphincterotomy (selective cannulation) of the bile duct is required. Occasionally special techniques and devices are required to gain access. Even with operator skill and experience, this procedure can be difficult. FIGS. 1A and 1B illustrate a front and cross-sectional side view, respectively of a papilla of Vater 50. The bile duct 52 and pancreatic duct 54 almost always exit at a common orifice 56 in the ampulla of Vater 50. Their union is variable but usually just proximal to the orifice 56 in the sphincter of Oddi 58. The anatomy of the site usually favors entry of the pancreatic duct 54 when cannulation is attempted. During the procedure, the operator must blindly probe the ampullary orifice 56 in the direction of the common bile duct 52 to gain entry.

Because of the anatomic variables and the minute size of the orifices 52, 54, common bile duct 52 cannulation is occasionally not possible. Furthermore, excess manipulation of the sphincteric mechanism 58, inadvertent pancreatic duct 54 cannulation, guide wire probing, and repeated injection into the pancreatic duct 54 while attempting to selectively cannulate the bile duct 52 greatly increases the risk of increase the risk of pancreatitis, a serious complication of ampullary cannulation. Another risk factor for pancreatitis can include the heat produced from electric cutting devices.

When ordinary measures for selective biliary duct 52 cannulation fail, several alternate methods can be used to increase success. Needle-knife sphincterotomy has been the predominant technique used. In this procedure, a heated wire is used as a knife. One drawback to this technique is that the needle knife is difficult to control and can provide an improperly placed and larger incision than is desired. Another method includes the use of the pre-cut papillotome, which includes a cutting wire exposed at the tip of the device. The cutting wire is used to incise into the roof of the papilla to expose the bile duct orifice to facilitate entry. More recently, another method has been described using a standard papillotome to pre-cut through to the bile duct with the papillotome in the pancreatic duct. In another method, the liver can be punctured and a guide wire passed through the bile duct 52 and papilla of Vater 50 into the duodenum where an endoscopist can gain assisted access. These methods can increase the risk of pancreatitis and other complications.

SUMMARY OF THE INVENTION

The biliary sphincter scissor is a miniature device for cutting tissue in a sphincterotomy procedure. The scissor can be inserted through an endoscope and can include a stationary cutting surface or blade and a moveable or actuated cutting surface or blade. The stationary blade is fixed relative to a distal end of a sheath and has a small size so as to fit into the papillary orifice. The actuated blade is opened and closed by an actuating mechanism, preferably with the blades opening in the distal direction. The scissor is fixed to a shaft having a sheath which surrounds that portion of the actuating mechanism extending from the proximal end of the device to the scissor. The shaft is flexible to accommodate the bends in an endoscope that has been inserted into the duodenum. The distal end of the shaft bends so that it can be directed through a side opening or aperture in the endoscope adjacent a viewing window. An elevator in the endoscope can be used to rotate the distal end of the scissor device relative to the endoscope axis. The actuator can include a wire attached to a control which pushes and pulls the wire to activate the actuating blade. The length and diameter of the device permits it to be passed through the working channel of an endoscopic device such as a duodenoscope.

In order to provide a desired orientation of the scissor with reference to the papilla when it protrudes from the duodenoscope, the distal end of the shaft can have a flexible arc-shaped curve. The curve defines a first plane which the surgeon can use to orient a second plane in which the scissors open and close. In a preferred embodiment, the plane in which the scissor blades function coincides with the plane of the curved shaft. In another preferred embodiment, the plane of scissor operation is oriented at an angle between 5 and 20 degrees relative to the plane defined by the curved shaft. A preferred embodiment can also include a rotationally stiff shaft such that the surgeon can rotate the handle of the device through a given arc and thereby cause rotation of the scissor plane through the same arc to achieve proper orientation of the blades relative to the papillary orifice.

The technique of biliary scissor sphincterotomy can include a series of steps following endoscopic placement of the scissor. The stationary blade of the scissor is inserted a short distance (2–3 mm) into the ampullary orifice. Usually there is only a short common channel after which the biliary and pancreatic ducts diverge. The scissor blade is directed toward the bile duct while remaining in the common channel. Next, the common channel is cut open with the scissor by movement of the actuated blade through the tissue. Then the lower blade of the opened scissor is advanced along the incised channel in the bile duct direction and small "nips" are made to expose the opening of the duct. It is expected that only a few millimeters, approximately 4–6 mm, need to be opened in this manner, allowing subsequent select biliary cannulation with a standard catheter, guide wire, or sphincterotome. Adapting the scissor device to apply an electric current to the tissue during cutting provides for cauterization of the tissue thus enabling for a more extensive sphincterotomy.

Pre-cutting with the biliary sphincter scissor eliminates or reduces the risk of pancreatitis by avoiding papillary manipulation, contrast injection, and heat from cutting devices. Significant bleeding is not likely owing to the presence of only minor vessels in the incised area and the need for only a short incision.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
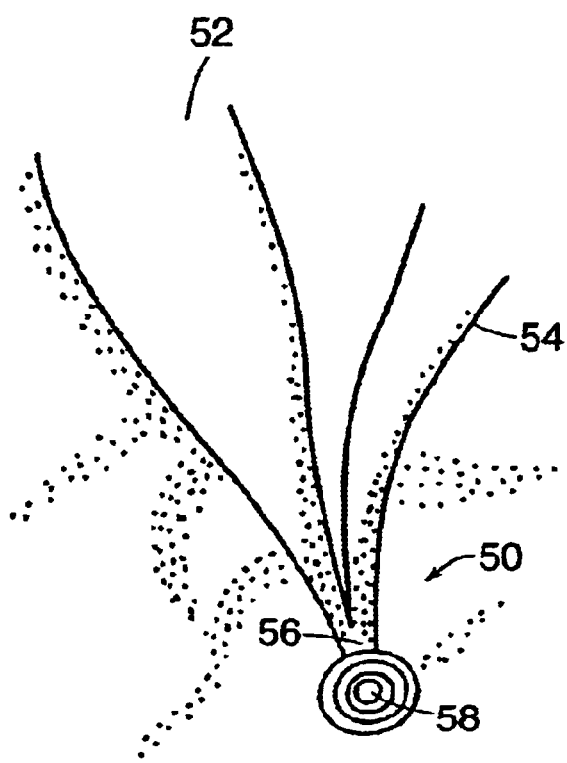
FIG. 1A shows a front sectional view of a papilla of Vater.
Figure 1B:
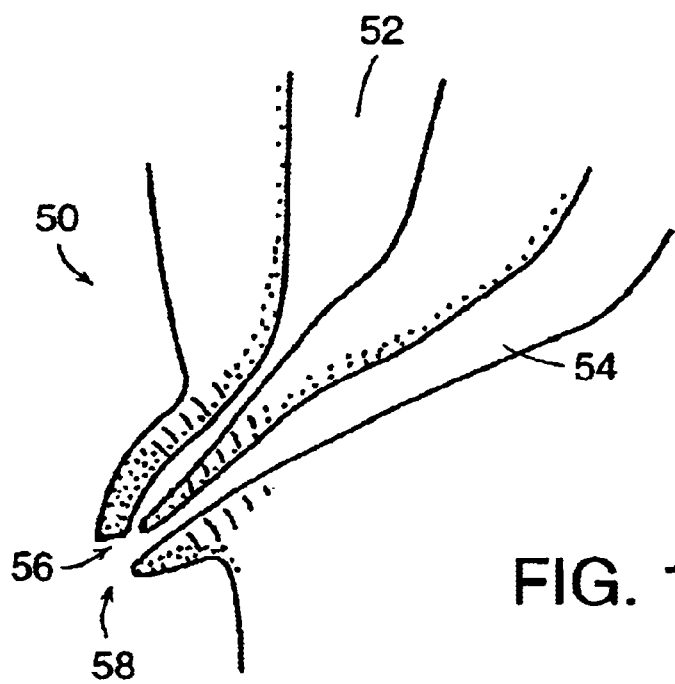
FIG. 1B shows a side sectional view of a papilla of Vater.
Figure 2A:
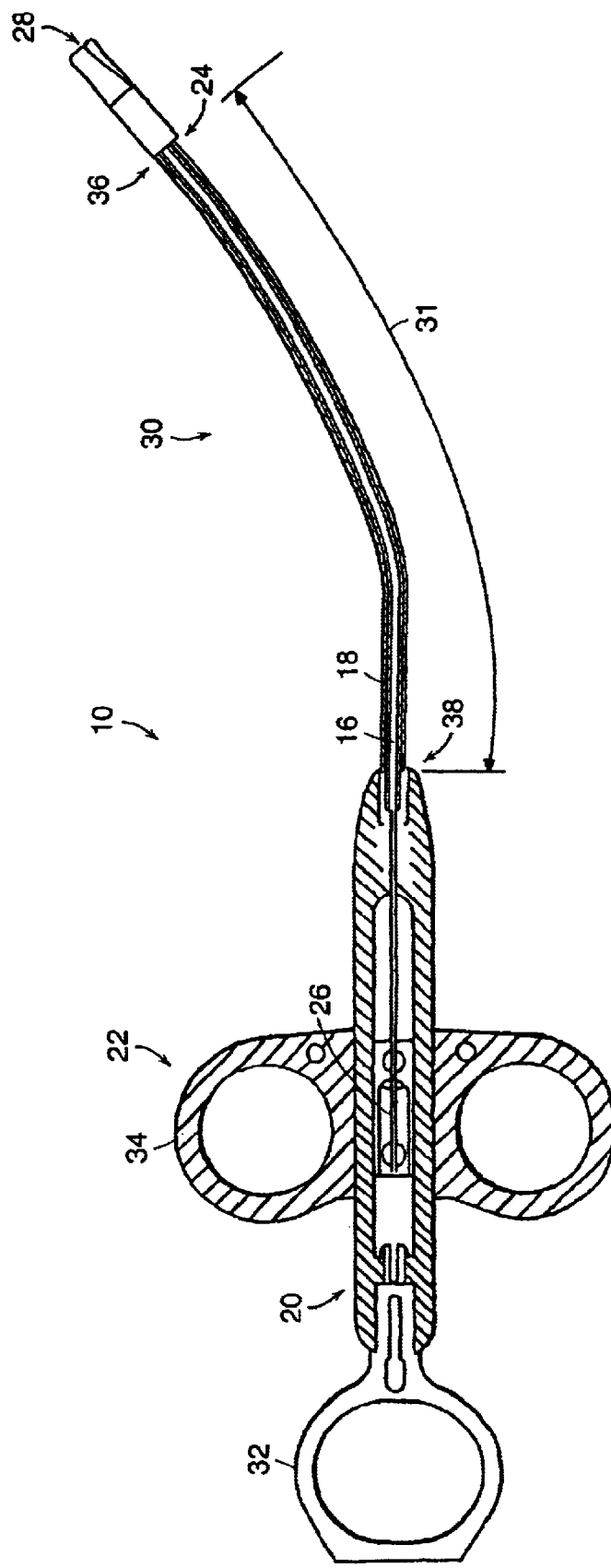
FIG. 2A illustrates biliary sphincter scissors.

FIG. 2A illustrates a pair of biliary sphincter scissors given generally as 10. The biliary sphincter scissors 10 have blades 28, which can include a stationary blade 12, and an actuated blade 14, an actuating mechanism 20 surrounded by a sheath 18, and a handle 22. The actuated blade 14 can be hingedly attached to the stationary blade 12. For example, the actuated blade 14 can be attached to the stationary blade 12 by a pin 40 which can act as a pivot point for the blade 14. Various blade lengths are appropriate. A cutting edge of about 0.150 inches is a minimal useful length. The cutting blade length is preferably in the range of 0.15 inches (3.81 mm) to 0.3 inches (7.62 mm). Open blade angles of between 25° and 90° can be used. The actuating blade 14 can have a thickness of approximately 0.025 inches (0.635 mm). The stationary blade 12 can have a thickness of approximately 0.035 inches (0.889 mm). The outer diameter of the scissors 10 can be 2.5 mm or less. Preferably the scissors 10 have a diameter between 1.5 to 2.0 mm. The sheath 18 can have a diameter smaller than that of the scissors 10.

During surgery, a user engages a biliary duct with the stationary blade 12 of the biliary sphincter scissors 10. To widen the opening of the biliary duct, a user can engage the actuated blade 14, thereby forcing the blade 14 into the papilla of Vater. The stationary blade 12 remains fixed within the biliary duct as the motion of the actuated blade 14 forces the papilla of Vater tissue between both the stationary 12 and actuated 14 blades. Such motion can cut the papilla of Vater. When used during a surgical procedure, it is preferred that the blade 14 be positioned at an oblique angle relative to the stationary blade 12 to allow for proper cutting of the papilla of Vater.

Figure 3:
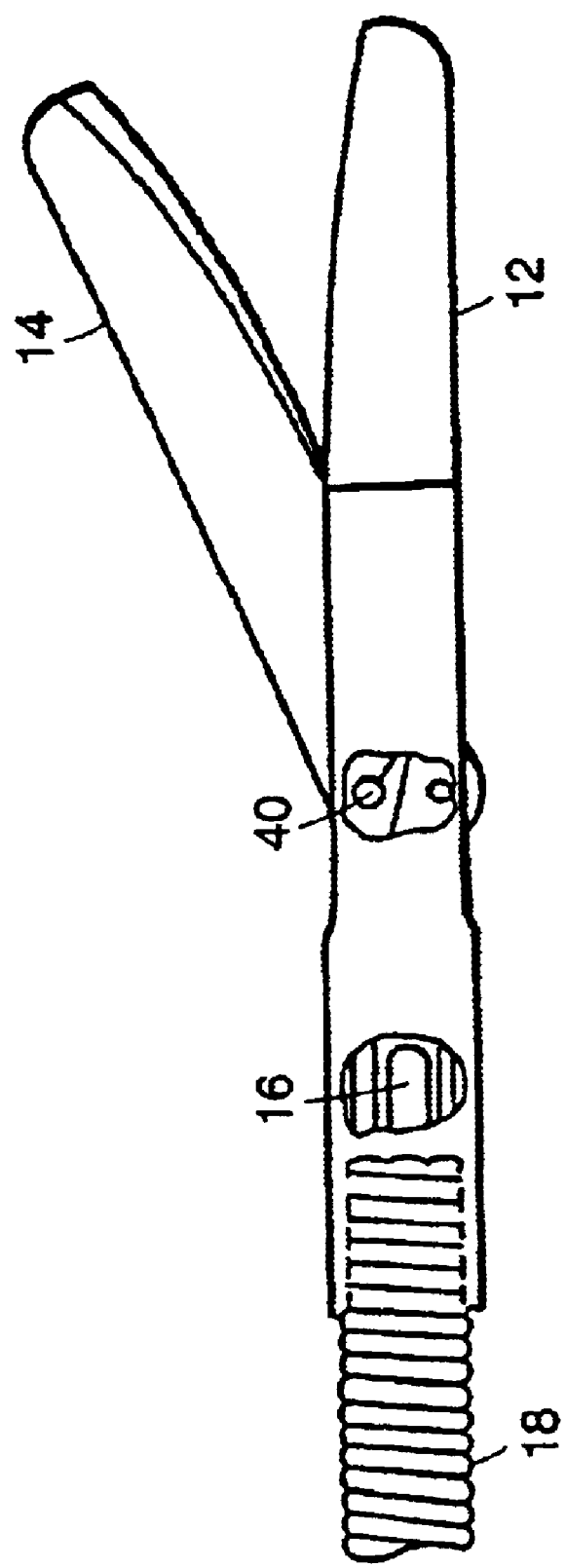
FIG. 3 illustrates a sectional view of the blades of biliary sphincter scissors.

The actuating mechanism 20 can include a wire 16 and a control 32. The wire 16 has a first end 24 and a second end 26. The first end 24 of the wire 16 can attach to the actuating blade 14, illustrated in FIG. 3. As the first end 24 of the wire 16 is pulled toward a user, the blade 14 can pivot on pin 40 relative to the stationary blade 12 to an open position. In an open position, the blade 14 forms an angle of at least 25° relative to the stationary blade 12. As the first end 24 of the wire 16 is pushed away from the user, the actuated blade 14 can pivot relative to the stationary blade 12 to a closed position. Such motion of the blade 14 can force the biliary sphincter scissors 10 to cut the papilla of Vater. The second end of the actuating mechanism 20 can be attached to the control 32. The control 32 can include a piston mechanism which allows a user to move the actuating blade 14.

The biliary sphincter scissors 10 include a housing or a handle 22 which can aid a user in controlling the motion of the actuating mechanism 20. The handle 22 can house the control portion 32 of the actuating mechanism 20. The handle 22, as shown in FIG. 2A, encases the control 32 and allows for the control 32 to slide both toward and away from the user to activate the actuated blade 14. The control portion 32 can include a loop, for example, to allow a user to manipulate the control 32 using his thumb. The handle 22 also includes a gripping element 34. The gripping element 34 allows the user to firmly grasp the biliary sphincter scissors 10 during a surgical procedure. The gripping element 34 can include rings, as shown in FIG. 2, through which the user can insert his fingers. The user can therefore have a firm grasp on the scissors 10 while having his thumb free to engage the control 32 of the actuating mechanism 20.

Figure 2B:
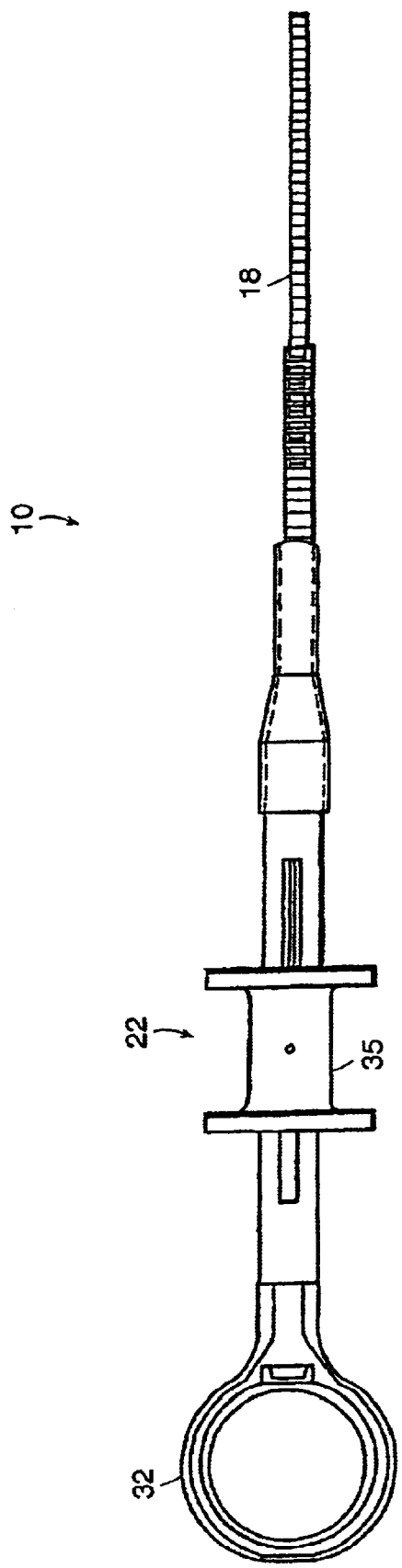
FIG. 2B illustrates an alternate handle for biliary sphincter scissors.

An alternate handle 22 is shown in FIG. 2B. The handle 22 includes a control element 32, as shown and described above, and a gripping element 35. The gripping element 35 allows the user to grasp the handle 22 between his index and middle fingers, for example, while manipulating the control 32 with his thumb. The biliary sphincter scissors 10 shown in FIG. 2A also includes a sheath 18 which covers the actuator 20. The sheath includes a first end 36 and a second end 38. The first end 36 of the sheath 18 is attached to the stationary blade 12. The second end 38 of the sheath 18 is attached to the handle 22 of the biliary sphincter scissors 10.

The sheath 18 can be made from several layers of materials. For example, the sheath can be made from a first layer of wound metal material and a second layer of coating material. The wound metal provides support for the actuating mechanism. The wound metal is sturdy enough and flexible enough to allow the biliary duct scissors to be introduced to a surgical site through an endoscope. The second layer of coating material can be made from a plastic or polytetrafluoroethylene, for example. The plastic can protect the metal layer from contamination within a biological environment and can also allow for the easy passage of the scissors 10 through an endoscope to a surgical site.

The sheath 18 forms a flexible arc-shaped curve 30 at the first end 36 of the sheath 18. The arc-shaped curve 30 of the sheath 18 can be formed by a process of bending and straining the sheath material, heating the bent material and allowing the bent material to cool. Such a process can be repeated until the desired curvature of the arc-shaped curve 30 is achieved. The arc-shaped curve 30 forces the stationary blade 12, the actuating blade 14 and the actuating mechanism 20 into a position which is almost perpendicular to the motion of the actuating mechanism 20 within the sheath 18.

The arc-shaped curve 30 allows the user to more easily orient the device in the appropriate direction. The scissor mechanism can be mounted on the sheath at various angles relative to a plane made by the arc-shaped curve. This allows for the most ideal axis of incision. The arc-shaped curve 30 is deformable which allows the biliary sphincter scissors 10 to travel through an endoscope without snagging. The length of the sheath 18 can be 120 cm, approximately 47 inches, from the point where the sheath 18 joins the handle 22 to the point where the sheath 18 joins the blades 28. The curve 30 of the sheath 18 when not deployed in an endoscope has an angle of at least 150° and is preferably in the range 150 degrees and 120 degrees relative to the axis of the non-curved portion of the sheath 18 to aid in positioning of the device.

Figure 5:
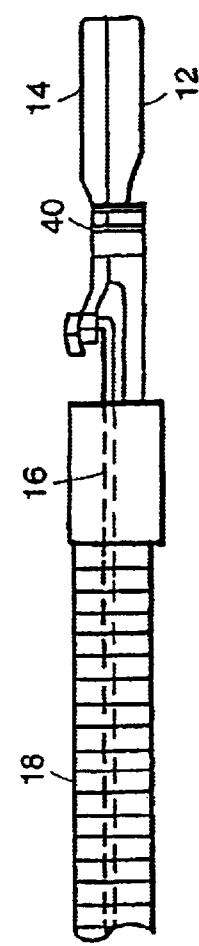
FIG. 5 shows a top view of a mounting for actuating and stationary blades of biliary sphincter scissors.
Figure 4A:
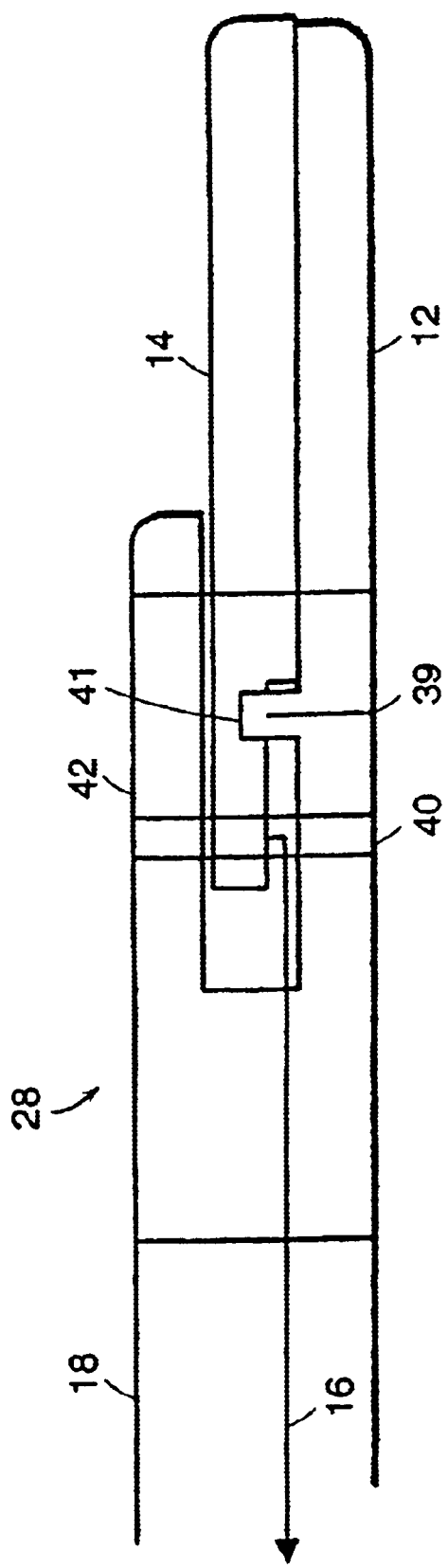
FIG. 4A shows a top view of the biliary sphincter scissors of FIG. 3.
Figure 4B:
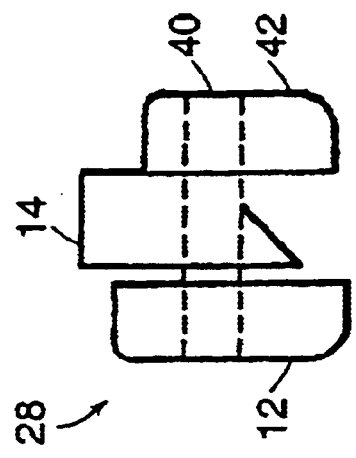
FIG. 4B shows a front view of the biliary sphincter scissors of FIG. 3.

FIGS. 4A and 4B illustrate a top and front view of the blades 28 of a pair of biliary duct scissors 10, respectively. FIGS. 4A and 4B show actuating blade 14 mounted between the stationary blade 12 and a mounting bracket 42. The mounting pin 40 can be used to secure the components 14, 12, 42 together. Both the stationary blade 12 and the mounting bracket 42 can be formed from a single piece of material. Also, both the stationary blade 12 and the mounting bracket 42 can be attached to the sheath 18. Alternately, as shown in FIG. 5, actuated blade 14 can be mounted directly to stationary blade 12 with mounting pin 40. The wire 16 can attach to the blade 14 to control the positioning of the blade 14. The thickness of the wire attachment can be 0.015 inches.

Figure 6A:
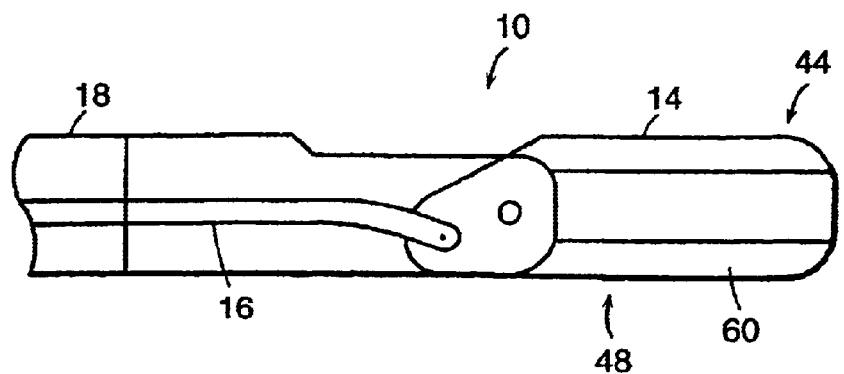
FIGS. 6A, 6B and 6C illustrate biliary sphincter scissors having a full stationary blade.
Figure 6B:
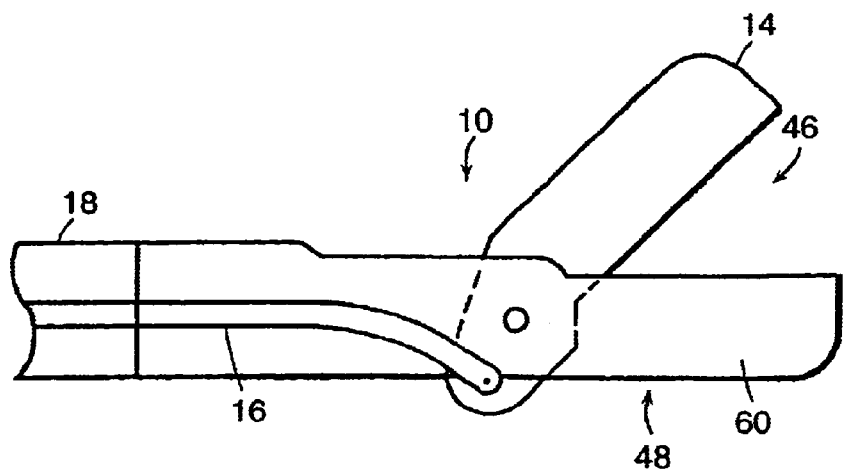
Figure 6C:
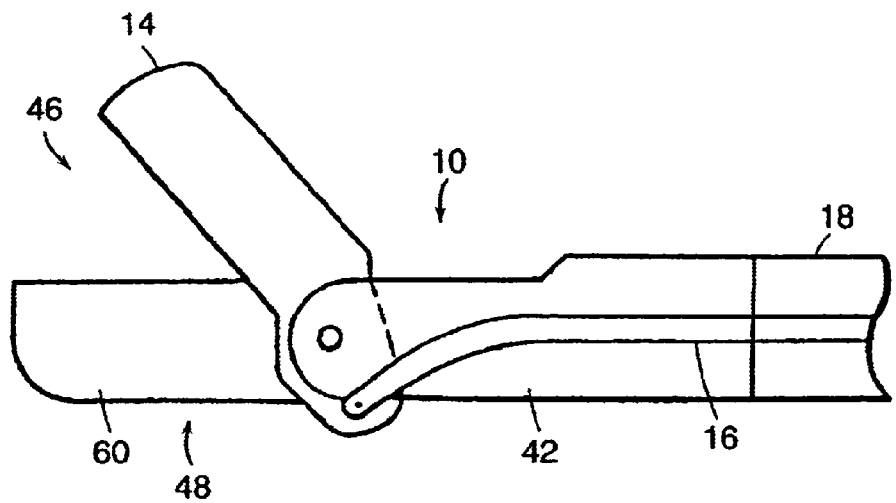
Figure 7A:
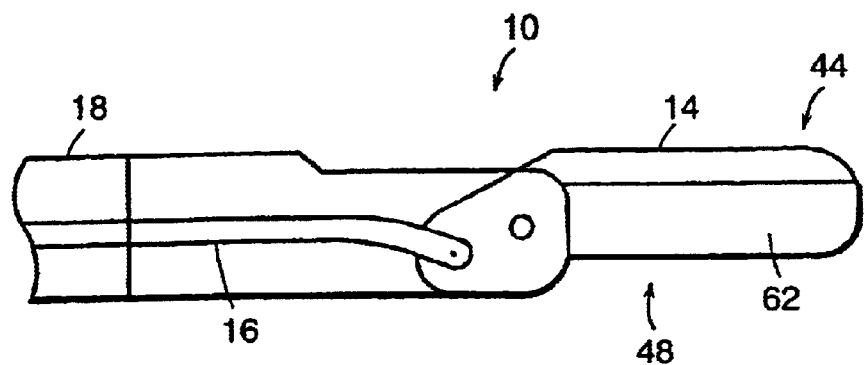
FIGS. 7A, 7B and 7C illustrate biliary sphincter scissors having a narrow stationary blade.
Figure 7B:
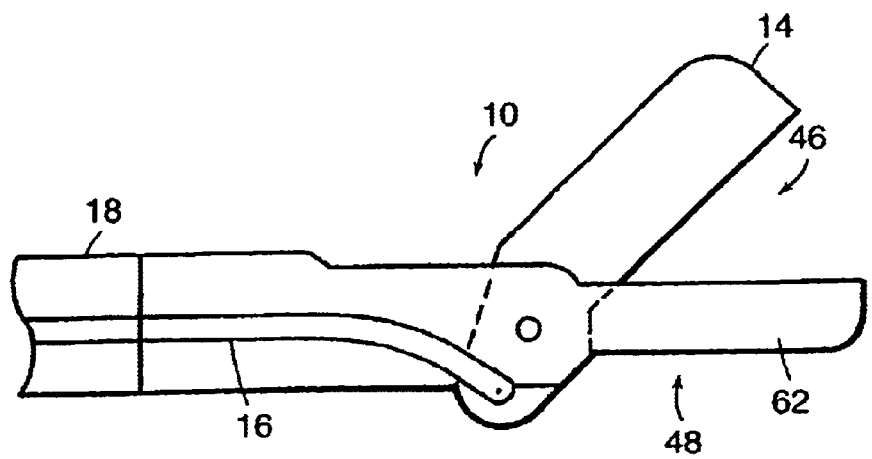
Figure 7C:
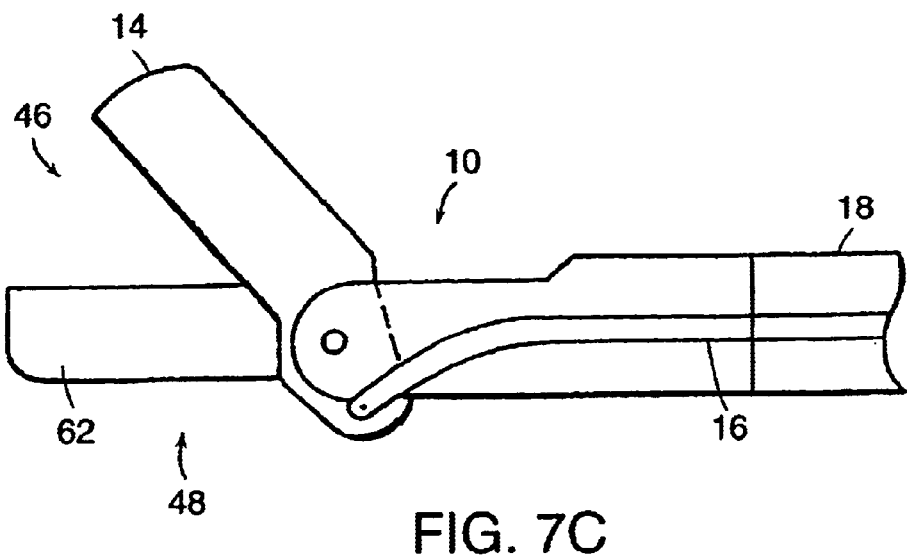
Figure 8A:
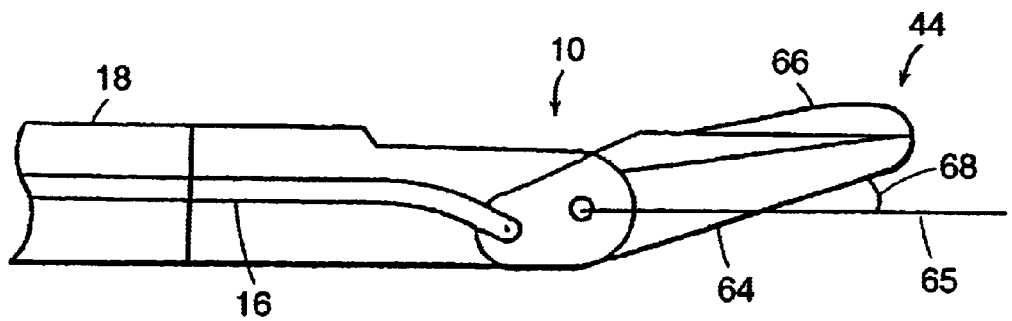
FIGS. 8A, 8B and 8C illustrate biliary sphincter scissors having angled blades.
Figure 8B:
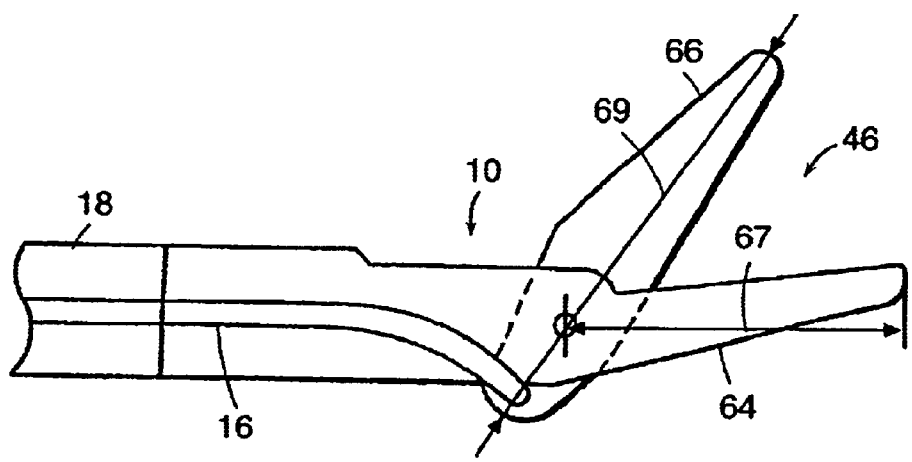
Figure 8C:
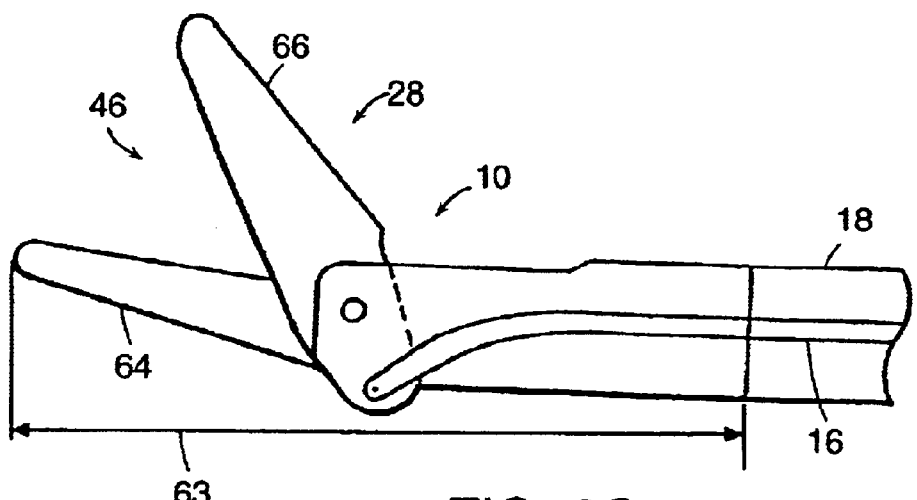

FIGS. 6, 7 and 8 illustrate various types of blades 28 that can be used as part of the biliary sphincter scissors 10. FIGS. 6A, 7A and 8A show the scissors 10 in a closed position 44 while FIGS. 6B, 7B and 8B and 6C, 7C and 8C show the scissors 10 in an open position 46. FIGS. 6B, 7B and 8B show a view of the scissors 10 from the stationary blade 12 direction while FIGS. 6C, 7C and 8C show a view from the mounting bracket 42 direction.

FIGS. 6A, 6B and 6C illustrate a pair of biliary sphincter scissors 10 having a full stationary blade 60. A full stationary blade 60 can have a bottom portion 48 which is continuous along the length of the stationary blade 60. Such continuity can allow for insertion of the stationary blade 60 within a papilla of Vater to perform a sphincterotomy.

FIGS. 7A, 7B and 7C show a pair of biliary sphincter scissors 10 having a narrow stationary blade 62. The narrow stationary blade 62 can have a bottom portion 48 which is not continuous along the length of the blade 62. A narrow stationary blade 62 can provide for insertion into a narrow common channel at the papilla of Vater.

FIGS. 8A, 8B and 8C illustrate a pair of biliary sphincter scissors 10 having a tapered stationary blade 64 and an angled actuated blade 66. The taper along the stationary blade 64 and the angle of the actuated blade 66 allows a user to cut into the papilla of Vater at an angle. Such an angle can prevent the user from having to over manipulate the scissors 10 for insertion into the area of the papilla of Vater, thereby facilitating proper positioning. The tapered stationary blade 64 can have a thickness of 0.035 inches (0.889 mm) and a length 67 of 0.215 inches (5.461 mm). The cutting edge of the stationary blade 64 can have a length of between 0.150 (3.81 mm) and 0.165 inches (4.191 mm). The stationary blade 64 can form an angle 68 of approximately 13° with respect to a horizontal 65. The angle 68 can be between 10° and 15°. The angled actuated blade 66 can have a thickness of 0.025 (0.635 mm) inches and a length of 0.215 inches (5.461 mm). The length 69 of the actuating blade 66 from distal tip to proximal end can be approximately 0.312 inches (7.94 mm). The cutting edge of the actuating blade 66 can have a length of between 0.150 inches (3.81 mm) and 0.165 inches (4.191 mm). The length 63 of the scissors 28 from the distal tip to the portion where the scissors 10 meet the sheath 18 can be approximately 0.5 inches (12.7 mm).

Figure 9:
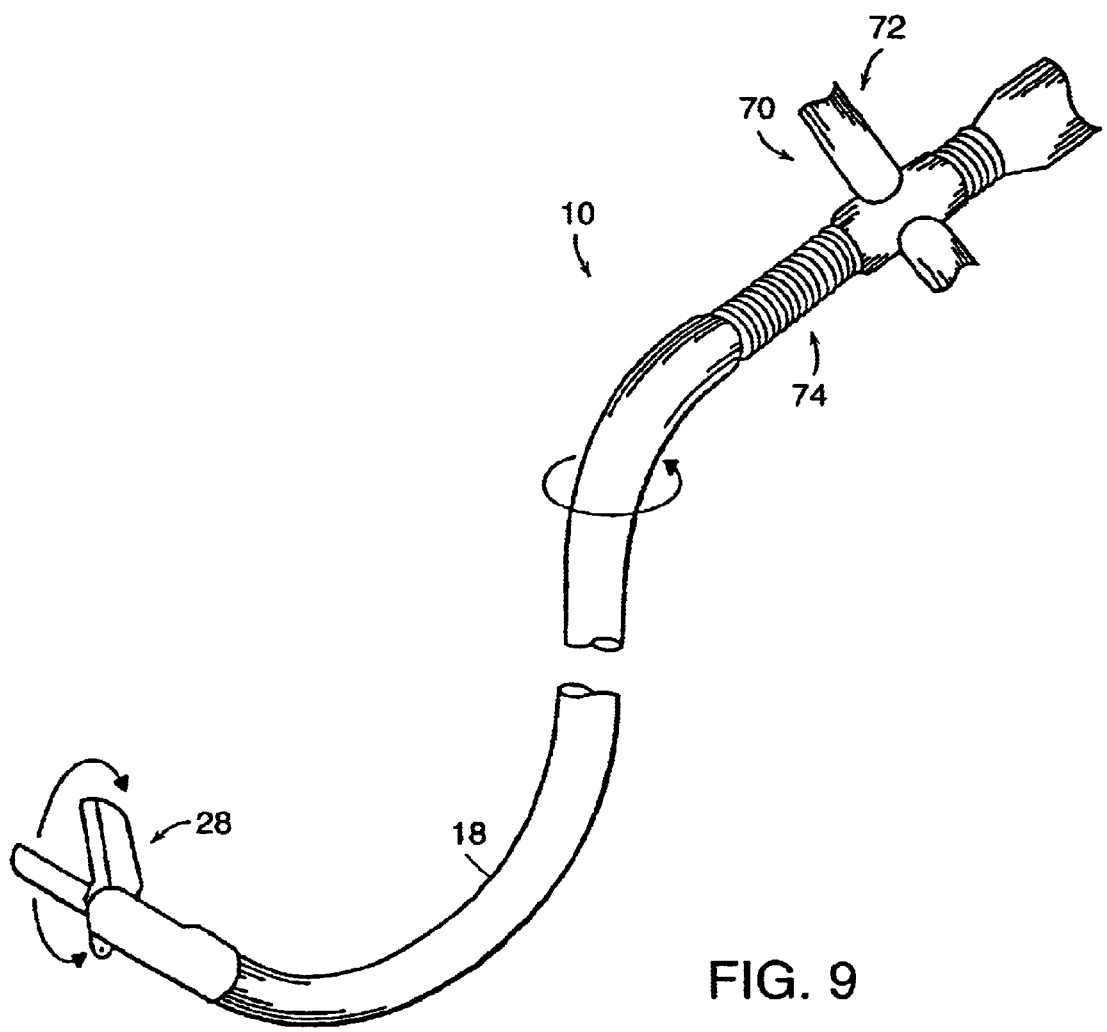
FIG. 9 illustrates biliary sphincter scissors having a torquing mechanism.

The biliary sphincter scissors 10 can also be designed for torqued positioning and can include a torque mechanism 70 in order to rotate the orientation of the blades 28 of the scissors 10 to a desired position. The torque mechanism 70 can include a torque bar 72 and a wire coil 74, as shown in FIG. 9. The wire coil 74 can be attached to both the torque bar 72 and the sheath 18. Rotation of the torque bar 72, in either a clockwise or a counter-clockwise direction, is transferred through the wire coil 74 and to the blade 28 at the end of the scissors 10. The wire coil 74 can be made from a material having a rotational stiffness that allows the rotation of the blades 28. Also, the sheath 18 can be made from a material that has a rotational stiffness which allows the rotation of the blades 28. Using the torque mechanism 70, the user can rotate the blades 28 prior to incising the papilla of Vater to ensure an accurate cut. Alternately, the handle 22 of the scissors 10 as shown in FIG. 2A, can be used as a torque mechanism to rotate the blades 28 of the scissors 10.

When performing an incision into the papilla of Vater, some minor bleeding can occur. Both the stationary blade 12 and the blade 14 can each include electrically conductive elements. When the conductive elements are engaged during cutting, a current from a current source can pass through the elements, thereby coagulating blood at the incision site during cutting. Such coagulation can eliminate or reduce any bleeding at the site.

Figure 10A:
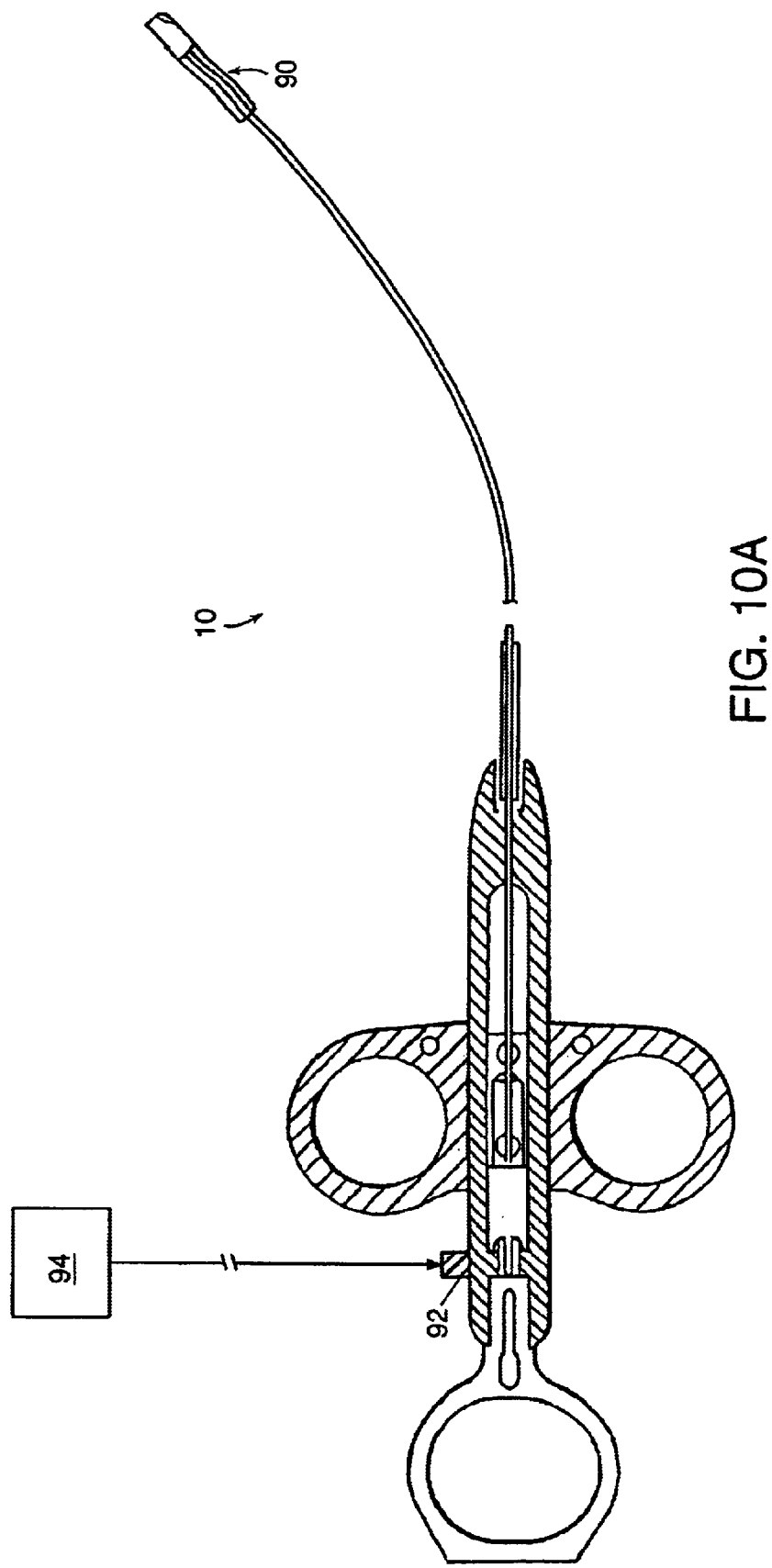
FIGS. 10A and 10B illustrate biliary sphincter scissors having electrical conductors for coagulating blood during incision.

FIG. 10A illustrates biliary sphincter scissors 10 having conductive elements 90. The scissors 10 can include a port 92 which allows connection of the elements 90 to a source 94. Preferably, the source 94 is an RF source. The port 92 can be located on the handle 22 of the scissors 10 to allow for ease of connection of the elements 90 to the source 94.

Figure 10B:
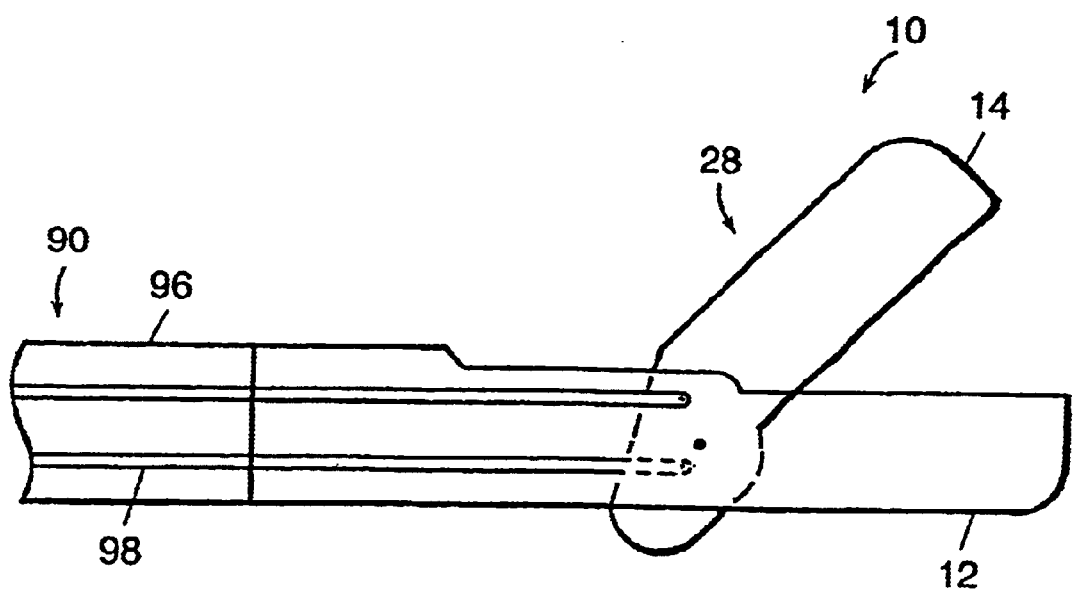

FIG. 10B shows conductive elements 90 attached to the blade 28 of the biliary sphincter scissors 10. The conductive elements 90 can include a first element 96 and a second element 98. The first element 96 can be attached to the actuating blade 14 while the second element can be attached to the stationary blade 12. When engaged, the elements 96, 98 can pass a current through the blades 28 during an incision procedure. The current can coagulate blood appearing at the incision site. An insulator is positioned between the blades at the hinged location to prevent shorting.

Figure 11:
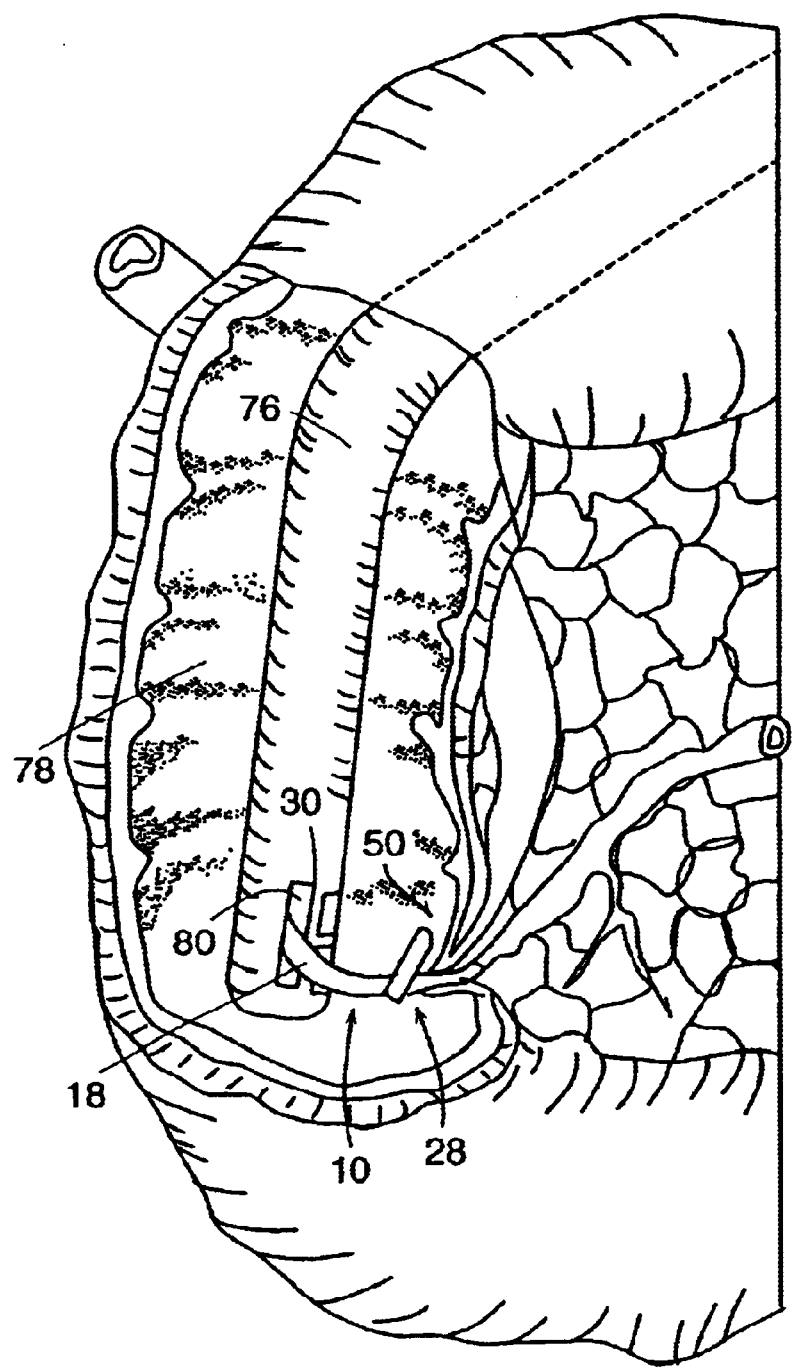
FIG. 11 shows biliary sphincter scissors used in an endoscope.

To use the biliary sphincter scissors 10 in an surgical procedure, the scissors 10 must be delivered to the papilla of Vater site using an endoscope 76, as shown in FIG. 11. The endoscope 76 can enter the duodenum 78 by way of oral entry into the patient. The endoscope 76 includes an opening 80 to allow the biliary sphincter scissors 10 to pass through the endoscope 76 and to the papilla of Vater 50. The biliary sphincter scissors 10 can be used in conjunction with a variety of duodenoscopes.

When the scissors 10 are moved through the opening 80 of the endoscope 76 during a procedure, a large portion of the arc-shaped curve 30 of the scissors 10 can be retained within the endoscope 76. The opening 80 can cause the curve 30 of the scissors to form an angle between 90° and 135° relative to the axis of the endoscope 76, as deployed in the duodenum. The endoscope 76 can include an elevator to control the angular positioning of the scissors. The curve 30 of the scissors 10 fixes the blades 28 of the scissors 10 within a single plane and in the correct orientation with respect to the papilla of Vater 50. The elevator in conjunction with an actuator within the endoscope 76 can control the angle at which the blades 28 engage and incise the papilla of Vater 50.

Figure 12:
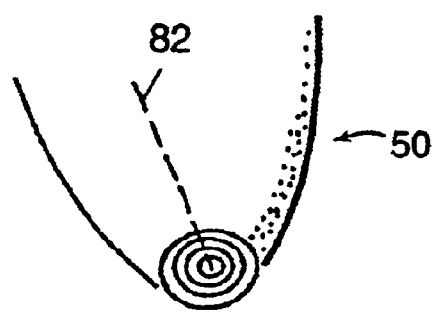
FIG. 12 illustrates the direction of an incision for a sphincterotomy.

When performing a sphincterotomy, the surgeon must incise the papilla of Vater through the common channel 56 to expose both the bile duct 52 and the pancreatic duct. Such exposure allows proper cannulation of the bile duct 52. The papilla of Vater is incised along the cutting axis 82 as shown in FIG. 12.

Figure 13A:
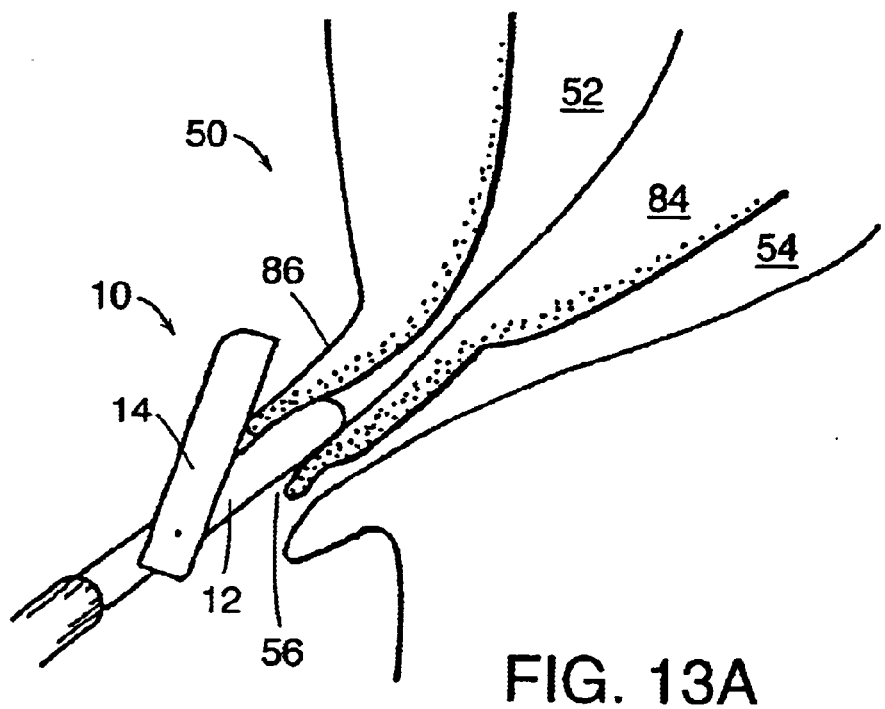
FIGS. 13A–13D illustrate a first cut in a sphincterotomy using biliary sphincter scissors.
Figure 13B:
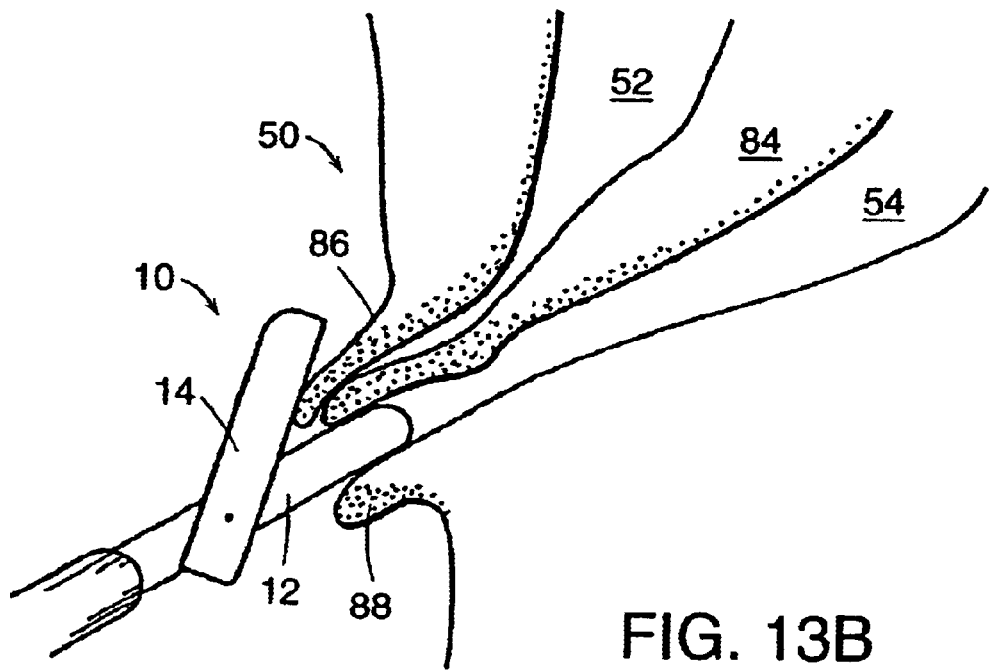

FIGS. 13A and 13B show a pre-cut being made into the papilla of Vater by the biliary sphincter scissors 10 to expose the bile duct 52. The stationary blade 12 of the scissors 10 can enter the common channel 56 and only has to be inserted a short distance, usually 2–3 mm. A septum 84 is located between the bile duct 52 and the pancreatic duct 54. The stationary blade 12 can enter or be directed toward the bile duct 52 through the common channel 56, as shown in FIG. 13A, such that the stationary blade 12 rests between the septum 84 and a top portion 86 of the papilla of Vater 50. The stationary blade 12 can be directed through the common channel 56 and into the pancreatic duct 54, as shown in FIG. 13B, such that the stationary blade 12 is located between a lower portion 88 of the papilla of Vater 50 and the septum 84. In either case, the actuated blade 14 can then cut into the papilla 50 using a small cut or nip along the cutting axis 82 to expose the bile duct 52 for cannulation.

Figure 13C:
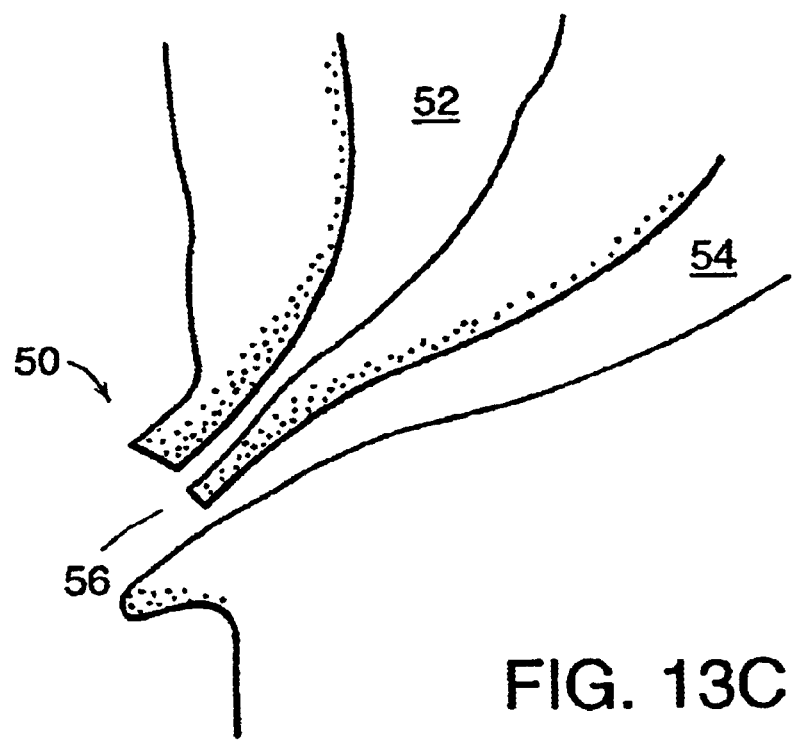
Figure 13D:
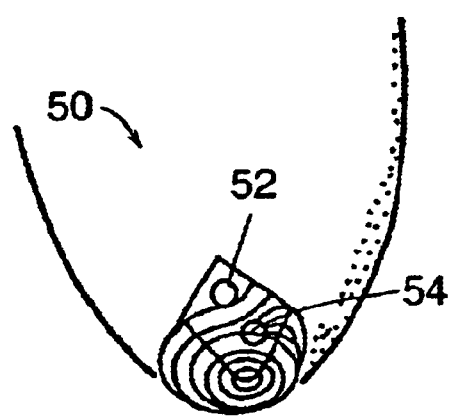

The cut made with the biliary sphincter scissors 10 exposes the separate orifices of the bile duct 52 and the pancreatic duct, shown in FIGS. 13C and 13D. Such exposure can provide for ease of cannulation of the bile duct 52.

Figure 14A:
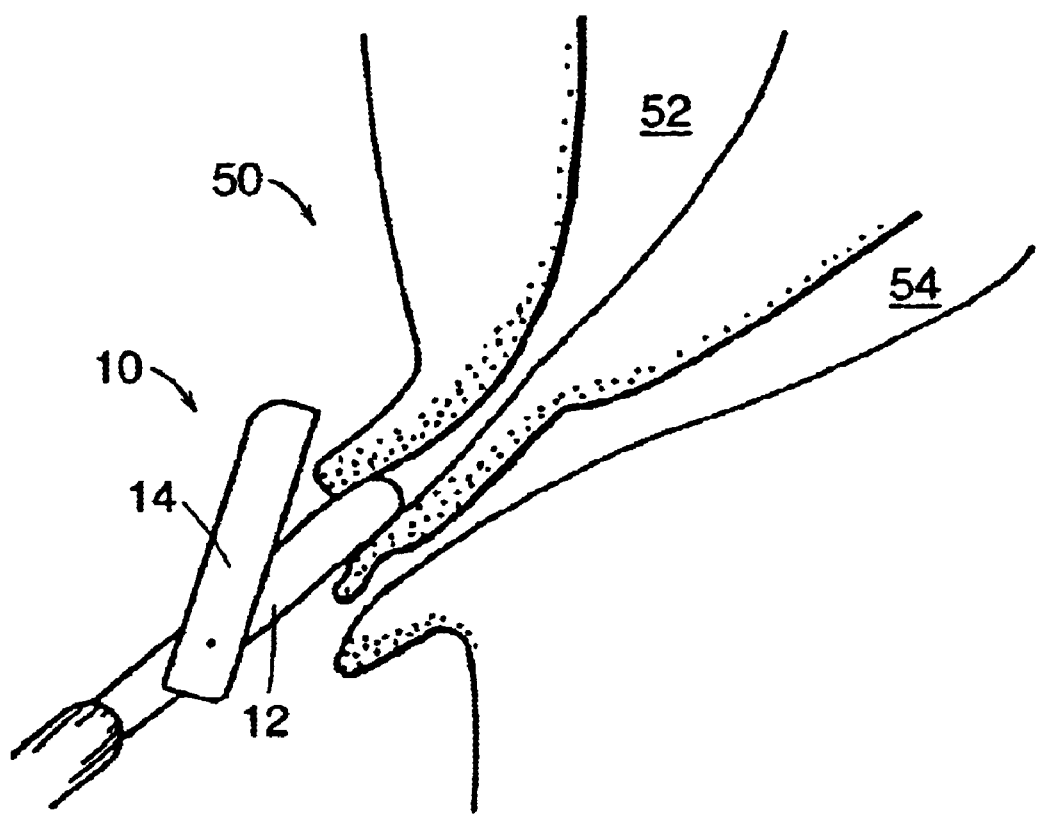
FIGS. 14A–14C show a second cut in a sphincterotomy using biliary sphincter scissors.
Figure 14B:
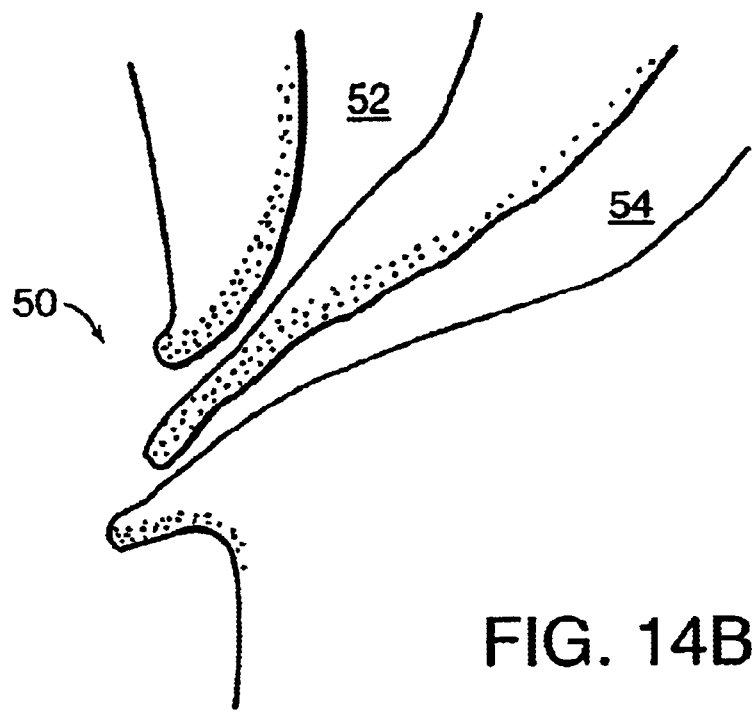
Figure 14C:
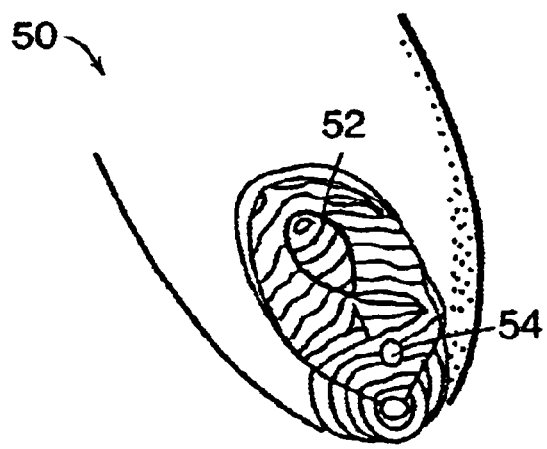

FIG. 14A shows the re-introduction of biliary sphincter scissors 10 into the bile duct 52. Such re-insertion is optional and can be done to further incise the papilla of Vater 50 so as to allow for a greater exposure of the bile duct 52, shown in FIGS. 14B and 14C. Once the bile duct 52 has been exposed, a user can insert a cannula into the bile duct to proceed with the sphincterotomy.

The biliary sphincter scissors 10 can be reusable or can be disposed of after a single use. Disposability of the scissors 10 can prevent risk of contamination in other patients.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of cutting tissue to expose a biliary duct comprising:
   providing a biliary sphincter scissor and an endoscope;
   positioning the endoscope at a surgical site;
   introducing the biliary sphincter scissor through the endoscope to the papilla of Vater;
   rotating a distal end of the biliary spincter scissor with an endoscopic elevator to position a first blade and a second blade and of the scissor relative to the surgical site;
   opening the first blade relative to the second blade while advancing the opened scissor towards the papilla of Vater; and
   incising the papilla of Vater with the scissor to expose the biliary duct.
   incising the papilla of Vater to expose the biliary duct.

2. The method of claim 1 further comprising:
   reintroducing the biliary sphincter scissor to the papilla of Vater; and
   further incising the papilla of Vater to further expose the biliary duct and the pancreatic duct.

3. The method of claim 1 further comprising:
   viewing a sphincterotomy site through a side viewing port of the endoscope;
   incising the sphincterotomy site with the biliary sphincter scissor to expose a bile duct opening; and
   cannulating the bile duct.

4. The method of claim 3 further comprising:
   providing a flexible sheath having a curved distal portion such that the distal portion of the sheath defines a plane of orientation.

5. The method of claim 1 further comprising actuating relative movement between the first blade and the second blade with a manually operated handle.

6. The method of claim 1 further comprising:
   providing biliary sphincter scissors having a stationary blade that extends along a distal longitudinal axis of a sheath that is connected to the biliary sphincter scissors, and an actuated blade that moves relative to the longitudinal axis between an open position and a closed position.

7. The method of claim 6 further comprising:
   providing a control wire extending within the sheath to a handle having an actuator that controls movement of the actuated blade.

8. A method of facilitating biliary cannulation comprising:
   providing an endoscope and a biliary sphincter scissor having a stationary blade that extends along a distal longitudinal axis of a sheath that is connected to the biliary sphincter scissor, and an actuated blade that moves relative to the longitudinal axis between an open position and a closed position;
   positioning the endoscope at a surgical site;
   introducing the biliary sphincter scissor through the endoscope to the papilla of Vater;
   introducing the stationary blade through the ampullary orifice;
   incising the papilla of Vater to expose the biliary duct thereby facilitating biliary cannulation.

9. The method of claim 8 further comprising using a torque mechanism to rotate the blades of the biliary sphincter scissors.

10. The method of claim 8 further comprising:
    reintroducing the biliary sphincter scissors to the ampullary orifice; and
    further incising the papilla of Vater to further expose the biliary duct and the pancreatic duct.

11. The method of claim 8 further comprising bending a distal portion of the sheath at an angle between 90° and 135° relative to an endoscopic axis.

12. The method of claim 8 further comprising cannulating the bile duct.

13. The method of claim 8 further comprising disposing of the biliary sphincter scissor after a single procedure.

14. The method of claim 8 further comprising sterilizing the biliary sphincter scissor after a procedure for use in a second procedure.

15. A method of exposing an opening of a biliary duct comprising:
    providing an endoscope and a biliary sphincter scissors having a stationary blade that extends along a distal longitudinal axis of a sheath that is connected to the biliary sphincter scissors, and an actuated blade that moves relative to the longitudinal axis between an open position and a closed position;
    positioning the endoscope at a surgical site;
    introducing the biliary sphincter scissors through the endoscope to the papilla of Vater;
    introducing the stationary blade into a common canal;

moving the actuated blade to cut the papilla of Vater to open the common canal;

advancing the stationary blade in the opened common canal; and exposing the opening of the biliary duct.

16. The method of claim 15 further comprising using a torque mechanism to rotate the blades of the biliary sphincter scissors.

17. The method of claim 15 further comprising advancing the stationary blade towards the bile duct.

18. The method of claim 15 further comprising cannulating the bile duct.

19. The method of claim 15 further comprising disposing of the biliary sphincter scissor after a single procedure.

20. The method of claim 15 further comprising sterizlizing the biliary sphincter scissor.

21. The method of claim 15 further comprising the stationary blade with an electrically conductive element.

22. The method of claim 15 further comprising providing the stationary blade and the actuated blade with electrically conductive elements.

23. The method of claim 22 further comprising conducting a current with the electrically conductive elements.

24. The method of claim 22 further comprising coagulating blood with the scissor.

25. A method of using a biliary sphincter scissors comprising:

providing an endoscope and a biliary sphincter scissors having a stationary blade that extends along a distal longitudinal axis of a sheath that is connected to the scissors, and an actuated blade that moves relative to the longitudinal axis between an open position and a closed position;

positioning the endoscope at a surgical site;

introducing the biliary sphincter scissors through the endoscope to the papilla of Vater;

introducing the stationary blade through the ampullary orifice into a common canal;

cutting open the common canal by the movement of the actuated blade through the tissue; and removing the biliary sphincter scissors from the endoscope.

26. The method of claim 25 further comprising disposing of the biliary sphincter scissors after a single procedure.

27. The method of claim 25 further comprising sterilizing the biliary sphincter scissors.

28. The method of claim 25 further comprising providing the stationary blade and the actuated blade include electrically conductive elements.

29. The method of claim 28 further comprising coagulating blood with the scissor.

30. The method of claim 25 further comprising using a torque mechanism to rotate the blades of the biliary sphincter scissors.

31. The method of claim 25 further comprising advancing the stationary blade towards the bile duct.

* * * * *